(12) United States Patent
Lotze et al.

(10) Patent No.: US 9,301,825 B2
(45) Date of Patent: Apr. 5, 2016

(54) BODILY IMPLANTS FORMED FROM DIFFERENT MATERIALS

(75) Inventors: Peter Lotze, Missouri City, TX (US); Maya Matusovsky, Waltham, MA (US); Steven A. Olivieri, Shrewsbury, MA (US); Curt R. Powell, Tulsa, OK (US); Scott E. Litwiller, Tulsa, OK (US); James Goddard, Pepperell, MA (US); Peter J. Pereira, Mendon, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 122 days.

(21) Appl. No.: 13/542,195

(22) Filed: Jul. 5, 2012

(65) Prior Publication Data

US 2013/0178696 A1    Jul. 11, 2013

Related U.S. Application Data

(60) Provisional application No. 61/504,917, filed on Jul. 6, 2011.

(51) Int. Cl.
*A61F 2/02* (2006.01)
*A61F 2/00* (2006.01)

(52) U.S. Cl.
CPC ............. *A61F 2/0045* (2013.01); *A61F 2/0063* (2013.01); *A61F 2240/001* (2013.01); *A61F 2250/0014* (2013.01)

(58) Field of Classification Search
CPC ..... A61F 2/004; A61F 2/0045; A61F 2/0063; A61F 2/0036; A61F 2250/0014; A61F 2250/003; A61F 2250/0031; A61B 2017/00805

USPC ................................................. 600/29, 30, 37
See application file for complete search history.

(56) References Cited

U.S. PATENT DOCUMENTS 3,103,666 A    9/1963  Bone
4,829,999 A    5/1989  Auth
(Continued)

FOREIGN PATENT DOCUMENTS

WO    2005/110273 A1    11/2005
WO    WO 2006045042 A1 *    4/2006
(Continued)

OTHER PUBLICATIONS

Non-Final Office Action for U.S. Appl. No. 13/424,862, mailed Jan. 8, 2014, 11 pages.
(Continued)

*Primary Examiner* — Charles A Marmor, II
*Assistant Examiner* — Thaddeus Cox
(74) *Attorney, Agent, or Firm* — Brake Hughes Bellermann LLP

(57) ABSTRACT

In one embodiment, an implant includes a body member and an extension member. The body member is formed of a first material and has a first side portion and a second side portion. The extension member is formed of a second material different than the first material. The extension member has a first arm portion, a second arm portion, and a mid-portion disposed between the first arm portion and the second arm portion. The mid-portion extends from the first side portion of the body member to the second side portion of the body member. The first arm portion extends from the first side portion of the body member along a first axis. The second arm portion extends from the second side portion of the body member along a second axis different than the first axis.

15 Claims, 7 Drawing Sheets

(56) References Cited

U.S. PATENT DOCUMENTS

| | | |
|---|---|---|
| 5,085,661 A | 2/1992 | Moss |
| 5,307,924 A | 5/1994 | Manosalva et al. |
| 5,341,823 A | 8/1994 | Manosalva et al. |
| 5,531,678 A | 7/1996 | Tomba et al. |
| 5,531,699 A | 7/1996 | Tomba et al. |
| 5,601,571 A | 2/1997 | Moss |
| 5,647,874 A | 7/1997 | Hayhurst |
| 5,814,069 A | 9/1998 | Schulze et al. |
| 6,475,135 B1 | 11/2002 | Levy |
| 6,872,192 B2 | 3/2005 | Nash et al. |
| 2002/0087178 A1 | 7/2002 | Nobles et al. |
| 2002/0107430 A1* | 8/2002 | Neisz et al. ............... 600/37 |
| 2002/0123750 A1* | 9/2002 | Eisermann et al. ......... 606/69 |
| 2004/0039246 A1* | 2/2004 | Gellman et al. ............ 600/30 |
| 2004/0073233 A1 | 4/2004 | Jannot |
| 2009/0171143 A1 | 7/2009 | Chu et al. |
| 2010/0152530 A1* | 6/2010 | Timmer et al. ............. 600/37 |
| 2010/0268274 A1 | 10/2010 | Williams |
| 2010/0312043 A1* | 12/2010 | Goddard .................... 600/30 |
| 2011/0077456 A1* | 3/2011 | Drummond ................ 600/30 |
| 2011/0112357 A1* | 5/2011 | Chapman et al. .......... 600/37 |
| 2012/0240378 A1 | 9/2012 | Weiser et al. |

FOREIGN PATENT DOCUMENTS

| | | |
|---|---|---|
| WO | 2007/149348 A2 | 12/2007 |
| WO | 2013/006777 A1 | 1/2013 |

OTHER PUBLICATIONS

Search Report and Written Opinion for International Application No. PCT/US2012/045716, mailed Oct. 17, 2012, 18 pages.

International Preliminary Report on Patentability for International Application No. PCT/US2012/045716, mailed Jan. 16, 2014, 8 pages.

Non-Final Office Action Response or U.S. Appl. No. 13/424,862, filed on Apr. 8, 2014, 8 pages.

Final Office Action for U.S. Appl. No. 13/424,862, mailed on Jun. 25, 2014, 24 pages.

\* cited by examiner

BODILY IMPLANTS FORMED FROM DIFFERENT MATERIALS

CROSS REFERENCE TO RELATED APPLICATION

This application is a Nonprovisional of, and claims priority to, U.S. Provisional Application No. 61/504,917, filed on Jul. 6, 2011, entitled "BODILY IMPLANTS FORMED FROM DIFFERENT MATERIALS", which is incorporated by reference herein in its entirety.

TECHNICAL FIELD

This disclosure relates generally to medical devices and more particularly to implants configured to provide support within a body of a patient and methods for securing such implants with the body of the patient.

BACKGROUND

A variety of medical procedures are performed to treat various female pelvic dysfunctions, including procedures to treat urinary incontinence, and correcting various prolapse conditions such as uterine prolapse, cystoceles, rectoceles, and vaginal vault prolapse.

Women often experience vaginal prolapses due to age or other factors. For example, women may experience a cystocele, a rectocele and/or a hysterocele. A cystocele occurs when the bladder bulges into the vagina, and a rectocele occurs when the rectum bulges into the vagina. A hysterocele occurs when the uterus descends into the vagina. An enterocele (small bowel prolapse) can also occur, when the small bowel pushes through the upper wall of the vagina.

Treatments of such dysfunctions have included suturing procedures or the use of implants for support or suspension. A hysterocele is often treated with a hysterectomy followed by a vaginal vault suspension. Various devices and procedures are used to deliver and secure pelvic implants within a variety of different anatomical structures within a pelvic region. Implants can be delivered to a pelvic region through one or more vaginal incisions, and/or through exterior incisions in the patient.

Existing implants differ in many ways. For example, some implants are formed of a biologic material while others are formed or synthetic materials. Some biologic implants are known to breakdown within the body of the patient over time. Accordingly, in some cases, the patient can experience a recurrence of the dysfunction or prolapse condition. Some implants formed with synthetic materials may be more stable within the body of the patient, but may cause erosion of bodily tissue near the incision (for example, near the vaginal incision created to place the implant).

Accordingly, it is desirable to provide an implant that includes the advantages of both the biologic implants and the synthetic implants.

SUMMARY

In one embodiment, an implant includes a body member and an extension member. The body member is formed of a first material and has a first side portion and a second side portion. The extension member is formed of a second material different than the first material. The extension member has a first arm portion, a second arm portion, and a mid-portion disposed between the first arm portion and the second arm portion. The mid-portion extends from the first side portion of the body member to the second side portion of the body member. The first arm portion extends from the first side portion of the body member along a first axis. The second arm portion extends from the second side portion of the body member along a second axis different than the first axis.

DETAILED DESCRIPTION

Figure 1:
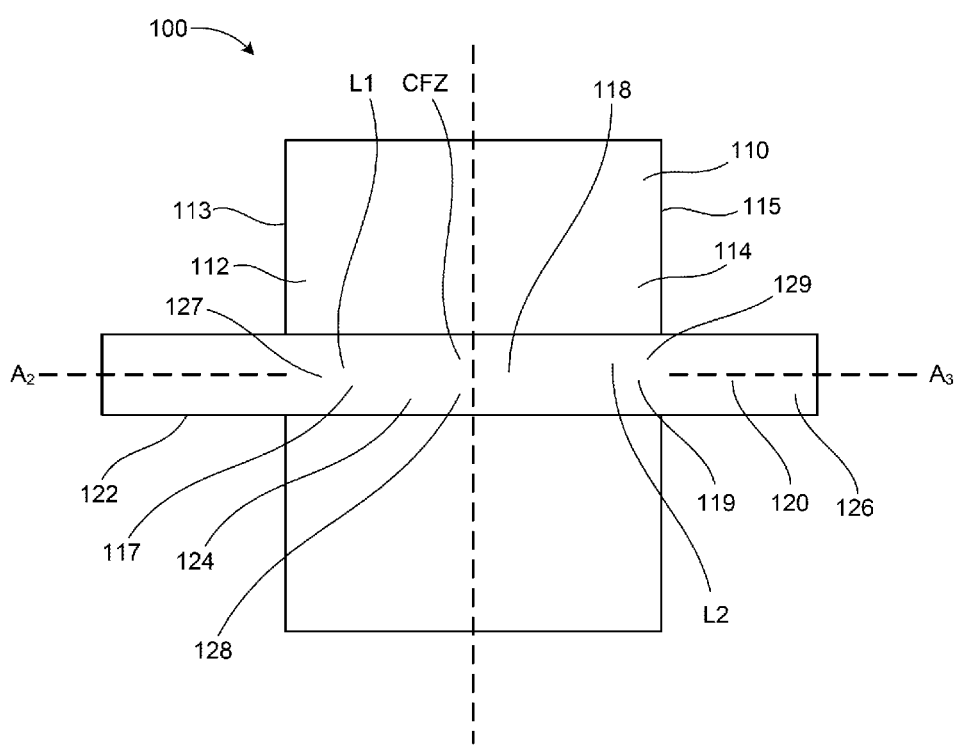
FIG. 1 is a schematic illustration of an implant according to an embodiment of the invention.

The devices and methods described herein are generally directed to implants (e.g., posterior support implants, anterior support implants, total pelvic floor repair implants) and the delivery and placement of such implants within a pelvic region (also referred to herein as "pelvis") of a patient. An implant can be placed into the pelvic space of a patient and secured at any of several locations within the pelvic space to treat many different female pelvic floor dysfunctions. For example, an implant can be secured to a sacrospinous ligament or a ureterosacral ligament for uterine preservation (e.g., if a prolapsed uterus is otherwise healthy, a hysterectomy is not preformed and the uterus is re-suspended with an implant), or for posterior support. In another embodiment, an implant can be secured to pubo-urethral tissue or an obturator muscle (e.g., internus or externus) or membrane (each also referred to herein as "obturator") to treat, for example, incontinence. In yet another embodiment, an implant can be secured to a sacrospinous ligament or an arcus tendineus fascia pelvis (i.e., white line) (also referred to herein as "arcus tendineus") for paravaginal repairs including, for example, cystoceles, rectoceles and enteroceles. An implant can also be secured to various combinations of such locations. A single implant or multiple implants can be used in a single procedure. In some applications, when multiple implants are used, support can be provided in desired areas and improved control of the direction of stretch or support of the implant can be achieved. Various delivery devices, delivery aids, and methods are also described for delivering and securing an implant assembly within the patient.

An implant according to an embodiment of the invention can be implanted, for example, through a vaginal incision, in a retro-pubic direction (behind the pubic bone), or in a pre-pubic direction (in front of the pubic bone). In other embodiments, an implant can be placed in the direction of other anatomical structures as desired. A procedure to deploy a pelvic implant can include vaginal incisions, such as an anterior vaginal incision and/or a posterior vaginal incision. In some embodiments, a procedure may include an exterior incision.

Various embodiments of implants are described herein. An implant can be delivered to a pelvic region of a patient using a variety of different delivery devices, only some examples of which are described herein. Various delivery aids are also described, some of which can be included as part of an implant (e.g., provided to a physician assembled) some of which can be assembled to an implant just prior to implantation. Such delivery aids are typically removed after placing one or more straps of an implant at a desired tissue securement location, leaving the strap to engage the tissue and support the support portion of the implant. For example, a sleeve or dilator assembly can be used to lead an implant or a strap of an implant through a tissue in an intracorporeal location (i.e., within the patient's body), such as the sacrospinous ligament or arcus tendineus. In other embodiments, a sleeve or dilator assembly can be used to lead an implant or a strap of an implant through a tissue and to an extracorporeal location (outside the patient's body), such as through an obturator membrane or muscle and out through an exterior incision in the patient.

In some embodiments, an implant can be associated to delivery aid, such as a sleeve assembly or dilator device, after such delivery aid has been placed within a pelvic region. For example, in an embodiment of an implant having multiple straps, prior placement of a delivery aid can help with coordinating and organizing the placement of the various straps. Placing a delivery aid within a pelvic region first also helps reduce handling of the implant which can reduce damage to the implant during an implantation procedure.

As used herein, the terms proximal portion or proximal end refer to the portion or end, respectively, of a device that is closest to a physician when performing a medical procedure, and the terms distal portion or distal end refer to the portion or end, respectively, of the device that is furthest from the physician during a medical procedure. For example, a distal end or portion of a sleeve assembly or dilator device as described herein refers to the end or portion of the device that is first inserted into a body of a patient during a medical procedure. The proximal end or portion is the end or portion of the device that is inserted into a body of the patient after the distal end or distal portion. The terms "trailing end" and "leading end" are also referred to herein and have similar meanings as proximal and distal, respectively. As used herein, the term "leading end" refers to the end of a device or apparatus that is inserted into a body first. The term "trailing end" refers to the end of the device or apparatus that is inserted into the body after the leading end.

FIG. 1 is a schematic illustration of an implant 100 according to an embodiment. The implant 100 includes a body member 110 and an extension member 120. The implant 100 is configured to be disposed within a body of a patient and to provide support to a portion of the body of the patient. For example, in some embodiments, the implant 100 is configured to be disposed within a pelvic region of a patient and is configured to provide support to a portion of the body of the patient (such as a bladder or a uterus of the patient).

In some embodiments, the implant 100 is configured to be disposed within the body of the patient such that the body member 110 is disposed adjacent to a portion of the body that is in need of support (such as a bladder or a uterus of the patient) and the extension member 120 is disposed within or coupled to bodily tissue to support the implant 100 within the body of the patient. For example, in some embodiments, the extension member 120 is configured to be disposed within or otherwise coupled to a sacrospinous ligament of a patient. While many of the embodiments of the implant described herein are described as being configured to be disposed within a female patient, in some embodiments, the implant is shaped and configured to be placed in a body of a male patient and is configured to provide support to a portion of a body of a male patient.

The body member 110 is formed of a first material and includes a first side portion 112 (having an edge 113) and a second side portion 114 (having an edge 115). The body member 110 may be of any size or shape suitable for the purpose of the implant. For example, for implants that are configured to support a bladder of a patient, the body member may be of one shape. The body member may be of a different shape in an implant that is configured to support a uterus or other portion of the body of the patient.

In some embodiments, the body member 110 is formed of a biologic or natural material. For example, in some embodiments, the body member 110 is formed of or includes bovine dermis. In other embodiments, the body member is formed of or includes porcine dermis, human cadaveric dermis, or another collagen source. In some embodiments, the body member 110 is formed of Xenform® or Repliform® as sold by Boston Scientific Corporation.

In other embodiments, the body member 110 is formed of another type of material. For example, in some embodiments, the body member 110 is formed of a synthetic material, such as a polypropylene mesh or another biocompatible synthetic or mesh material.

The extension member 120 has a first arm portion 122, a second arm portion 126, and a mid-portion 124 disposed between the first arm portion 122 and the second arm portion 126. The extension member 120 is coupled to the body member 110 such that the mid-portion 124 extends from the first side portion 112 of the body member 110 to the second side portion 114 of the body member 110.

The extension member 120 may be of any size or shape suitable for the specific purpose of the implant. For example, for implants that are configured to support a bladder of a patient, the extension member may be of one shape. The extension member may be of a different shape in an implant that is configured to support a uterus or other portion of the body of the patient. For example, in some embodiments, the first arm portion 122 is thicker or wider than the mid-portion 124. In other embodiments, the mid-portion 124 is thicker or wider than the first arm portion 122 or the second arm portion 126.

In some embodiments, the extension member 120 is formed of or includes a material that is different than the material that forms or is included in the body member 110. In some embodiments, the extension member 120 is formed of a synthetic material. For example, in some embodiments, the extension member 120 is formed of or includes a mesh material, such as a polypropylene mesh. In other embodiments, the extension member 120 is formed of material such as polyvinylidene fluoride (PVDF), polyethylene terephthalate (PET), nylon, or other biocompatible polymers. In other embodiments, the extension member 120 is formed of or includes a natural material.

The first arm portion 122 of the extension member extends from the first side portion 112 of the body member 110 in a first direction. In some embodiments, the first arm portion 122 extends from the first side portion 112 of the body member 110 along an axis A2 that is perpendicular to a longitudinal axis A1 defined the body member 110. In other embodiments, the first arm portion 122 extends from the first side portion 112 of the body member 110 along an axis that is not perpendicular to the longitudinal axis A1 defined by the body member 110.

The second arm portion 126 of the extension member 120 extends from the second side portion 114 of the body member 110 in a second direction. In some embodiments, the second direction is different than the first direction. For example, in some embodiments, the second direction and the first direction are opposite directions. In other embodiments, the first direction and the second direction are different directions but are not opposite directions.

In some embodiments, the second arm portion 126 extends from the second side portion 114 of the body member 110 along an axis A3 that is perpendicular to a longitudinal axis A1 defined the body member 110. In other embodiments, the second arm portion 126 extends from the second side portion 114 of the body member 110 along an axis that is not perpendicular to the longitudinal axis A1 defined by the body member 110.

In some embodiments, the first arm portion 122 and the second arm portion 126 of the extension member 120 are substantially linear. In other embodiments, the first arm portion and the second arm portion include curved portions. In some embodiments, the mid-portion 124 of the extension member is substantially linear. In other embodiments, the mid-portion 124 of the extension member includes a curved portion.

In some embodiments, the extension member 120 is coupled to the body member 110 such that a first surface of the extension member 120 is disposed adjacent to a first surface of the body member 110. In other words, the extension member 120 overlays or overlaps a portion of the body member 110. For example, in the illustrated embodiment, the extension member 120 overlays or overlaps a portion of the body member 110 between the edges 113 and 115 of the body member 110.

In some embodiments, the extension member 120 is coupled to the body member 110 at a first location L1 and at a second location L2 different from and spaced from the first location L1. For example, in some embodiments, the mid-portion 124 of the extension member 120 includes a first portion 127, a second portion 129, and a middle portion 128 disposed between the first portion 127 and the second portion 129. The first portion 127 is coupled to the body member 110 at a first coupling location 117 of the body member 110. The second portion 129 is coupled to the body member 110 at a second coupling location 119 of the body member 110. The middle portion 128 of the extension member 120 is disposed adjacent to the body member 110 but is not coupled to the body member 110. For example, in some embodiments, the middle portion 128 of the extension member 120 is not directly coupled to the body member 110. Accordingly, the implant 100 includes a coupling free zone CFZ (and the body member 110 includes a coupling-free location 118). In some embodiments, the coupling-free location 118 of the body member 110 is located along the longitudinal axis A1 defined by the body member 110.

The extension member 120 may be coupled to the body member 110 using any known method. In some embodiments, the extension member 120 is coupled to the body member 110 via a suture. In other words, the extension member 120 is sewn to or stitched to the body member 110. For example, in some embodiments, a sewing machine (or other type of machine) may be used to couple or sew the extension member 120 to the body member 110. In other embodiments, the extension member 120 is hand sewn to the body member 110. Any of a number of stitch patterns may be used to sew the extension member 120 to the body member 110. For example, a lock stitch, a zig zag stitch, or a custom stitch may be used. Additionally, any stitch density or thread size may be used to sew the extension member 120 to the body member 110.

In other embodiments, another method of coupling is used to couple the extension member 120 to the body member 110. For example, in some embodiments, a biocompatible adhesive is used to couple the extension member 120 to the body member 110. In other embodiments, a clip, such as a clip formed of polypropylene, a biocompatible staple, a rivet, or a button is used to couple the extension member 120 to the body member 110. In some embodiments, the extension member 120 is woven through openings defined by the body member 110 to couple the extension member 120 to the body member 110.

Although only one extension member is illustrated, in some embodiments, the implant includes more than one extension member. Additionally, although the extension member is illustrated and described as including a first arm portion and a second arm portion, in some embodiments, the extension member includes more than two arm portions. For example, the extension member may include any number of arm portions. In such embodiments, the arm portions may extend to different portions within the body of the patient. For example, in some embodiments, two arms may extend from the body member to the sacrospinous ligament of the patient and two arms may extend from the body member to the arcus tendentious of the patient. Also, in some embodiments, the extension member includes a single arm portion that extends from the body member.

In some embodiments, the first arm portion 122 and the second arm portion 126 of the extension member 120 include tangs or tanged portions that are configured to help retain the arm portions in place within the bodily tissue in which they are disposed. The terms "tanged" or "tangs" as used herein mean roughened or jagged edges or areas, such as can result from cutting a woven or knit mesh material. In other embodiments, the arm portions 122 and 126 include barbs, dimples and/or other protrusions configured to engage the bodily tissue of the patient to help retain the implant 100 in place within the body of the patient. In other embodiments, other mechanisms may be used to couple the arm portions 122 and 126 to the bodily tissue. For example, in one embodiment the arm portions 122 and 126 may be sewn with sutures to the bodily tissue.

In some embodiments, the body portion 110 is formed of a biologic material and the extension member 120 is formed of a synthetic material. In some embodiments, the biologic material of the body portion 110 is configured to breakdown (or be absorbed) within the body of the patient over time. In such embodiments, the synthetic material of the extension member would remain and provide some support to the body of the patient. In some such embodiments, the support provided by the synthetic extension member might help prevent the need for a follow-up procedure.

Figure 2:
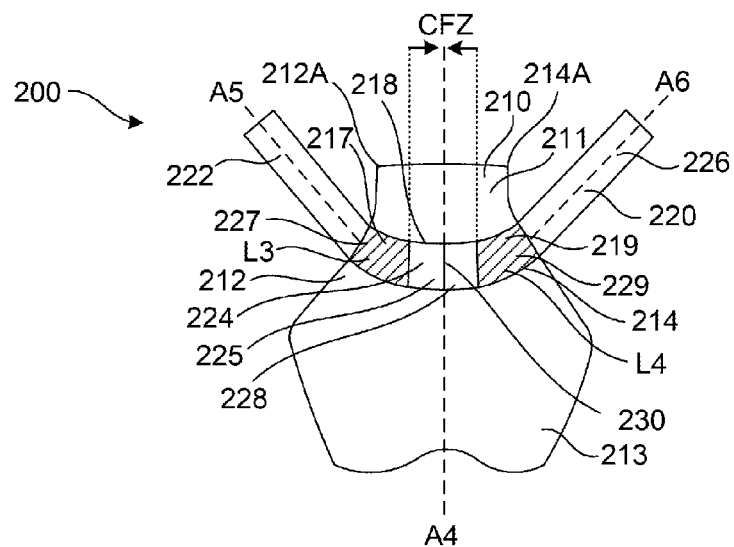
FIG. 2 is a top view of an implant according to an embodiment of the invention.
Figure 3:
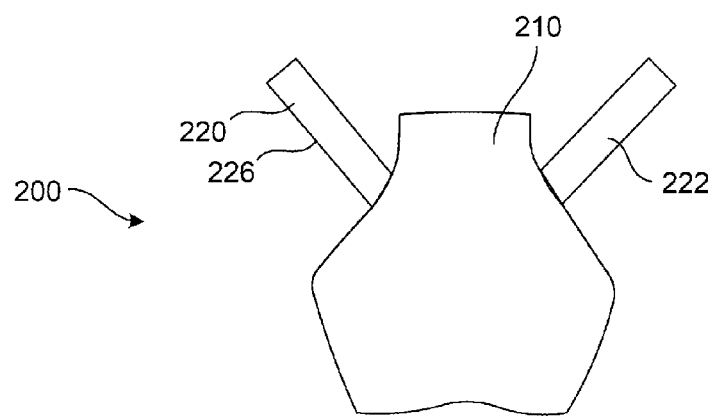
FIG. 3 is a bottom view of the implant of FIG. 2.

FIG. 2 is a top view of an implant 200 according to an embodiment. FIG. 3 is a bottom view of the implant 200. The implant 200 includes a body member 210 and an extension member 220. The implant 200 is configured to be disposed within a body of a patient and to provide support to a portion of the body of the patient. Specifically, the implant 200 is configured to be disposed in an anterior portion of a pelvic region of a patient. For example, the implant 200 may be placed in the anterior portion of a pelvic region of a patient and configured to support, for example, a bladder or a uterus of the patient. Specifically, the body member 210 may be disposed proximate the bladder and/or the uterus and the extension member may extend to the sacrospinous ligament of the patient to provide support to the implant 200 and to help retain the implant 200 in position within the body of the patient.

The body member 210 is formed of a first material and includes a first side portion 212 and a second side portion 214. Specifically, the body member 210 includes a first side edge 212A and a second side edge 214A. The body member 210 includes a narrow portion 211 disposed on one side of the extension member 120 and a wide portion 213 disposed on the other side of the extension member 220. Specifically, in the illustrated embodiment, the wide portion 213 includes side portions that have portions that extend out (away from a longitudinal axis A4 defined by the body member 210) and portions that extend in (toward the longitudinal axis A4). For example, in some embodiments, the wide portion 213 has a width of about 4 inches (about 10.2 cm) at its widest location. In other embodiments, the wide portion 213 has a width of less than 4 inches (about 10.2 cm). In yet further embodiments, the wide portion 213 has a width of more than 4 inches (about 10.2 cm).

In the illustrated embodiment, the body member 210 is formed of a biologic or natural material. For example, in some embodiments, the body member 210 is formed of or includes bovine dermis. In other embodiments, the body member 210 is formed of or includes porcine dermis, human cadaveric dermis, or another collagen source. In some embodiments, the body member 210 is formed of Xenform® or Repliform® as sold by Boston Scientific Corporation.

In other embodiments, the body member 210 is formed of another type of material. For example, in some embodiments, the body member 210 is formed of a synthetic material, such as a polypropylene mesh or another biocompatible synthetic or mesh material.

The extension member 220 has a first arm portion 222, a second arm portion 226, and a mid-portion 224 disposed between the first arm portion 222 and the second arm portion 226. The extension member 220 is coupled to the body member 210 such that the mid-portion 224 extends from the first side portion 212 of the body member 210 to the second side portion 214 of the body member 210. Specifically, in the illustrated embodiment, the extension member 220 extends from the first side edge 212A of the body member 210 to the second side edge 214A of the body member 210.

In some embodiments, the extension member 220 is formed of or includes a material that is different than the material that forms or is included in the body member 210. In the illustrated embodiment, the extension member 220 is formed of a synthetic material. For example, in some embodiments, the extension member 220 is formed of or includes a mesh material, such as a polypropylene mesh. In other embodiments, the extension member 220 is formed of or includes a natural material.

The first arm portion 222 of the extension member extends from the first side portion 212 of the body member 210 in a first direction. Specifically, the first arm portion 222 extends from the first side portion 212 of the body member 210 along an axis A5 that is non-perpendicular to a longitudinal axis A4 defined the body member 210.

In the illustrated embodiment, the second arm portion 226 extends from the second side portion 214 of the body member 210 along an axis A6 that is non-perpendicular to a longitudinal axis A4 defined the body member 210. The axis A6 is different and non-parallel to axis A5 defined by the first arm portion 222.

In the illustrated embodiment, the first arm portion 222 and the second arm portion 226 of the extension member 220 are substantially linear. Additionally, in the illustrated embodiment, the mid-portion 224 of the extension member 220 includes a curved portion 225.

The extension member 220 is coupled to the body member 210 such that a first surface of the extension member 220 is disposed adjacent to a first surface of the body member 210. In other words, as best illustrated in FIGS. 2 and 3, the extension member 220 overlays or overlaps a portion of the body member 210 (for example, the portion of the body member 210 between the first side edge 212A and the second side edge 214A). Specifically, the mid-portion 224 of the extension member 220 is on top of the body member 210 and visible in FIG. 2, but is below the body member 220 and not visible in FIG. 3. Accordingly, a physician may place the implant 200 within the body such that the body member 210 (rather than the side of the implant that includes the body member 210 and the extension member 220) is disposed adjacent or contacting the incision created to place the implant 200. In some embodiments, this may help reduce tissue erosion at or near the incision.

The extension member 220 is coupled to the body member 210 at a first location L3 and at a second location L4 different from and spaced from the first location L3. In the illustrated embodiment, the first location L3 and the second location L4 are disposed proximate opposite side portions 212 and 214 of the body member 210, respectively.

The mid-portion 224 of the extension member 220 includes a first portion 227, a second portion 229, and a middle portion 228 disposed between the first portion 227 and the second portion 229. The first portion 227 is coupled to the body member 210 at a first coupling location 217 of the body member 210. The second portion 229 is coupled to the body member 210 at a second coupling location 219 of the body member 210. The middle portion 228 of the extension member 220 is disposed adjacent to the body member 210 but is not coupled to the body member 210. Specifically, the middle portion 228 of the extension member 220 is not directly coupled to the body member 210. Accordingly, the implant 200 includes a coupling free zone CFZ (and the body member 210 includes a coupling-free location 218). In some embodiments, the coupling free zone is about 1 inch wide (about 2.5 cm). In other embodiments, the coupling free zone is larger than about 1 inch wide (about 2.5 cm).

In the illustrated embodiment, the coupling-free location 218 of the body member 210 is located along the longitudinal axis A4 defined by the body member 210. Accordingly, the coupling free zone CFZ of the implant 200 may be disposed within the body of the patient adjacent the incision location and/or the vaginal wall and may help prevent (or be less likely to cause) tissue erosion.

The extension member 220 may be coupled to the body member 210 using any known method. In the illustrated embodiment, the extension member 220 is sewn to the body member 210.

In the illustrated embodiment, the extension member 220 includes a centering mark 230. The centering mark or stripe 230 may be used to facilitate the accurate or correct placement of the implant 200 within the body of the patient. In some embodiments, the centering mark 230 is an ink stripe, such as a blue stripe. In other embodiments, the centering mark 230 is a different type of mark, such as a colored suture or the like.

Figure 4:
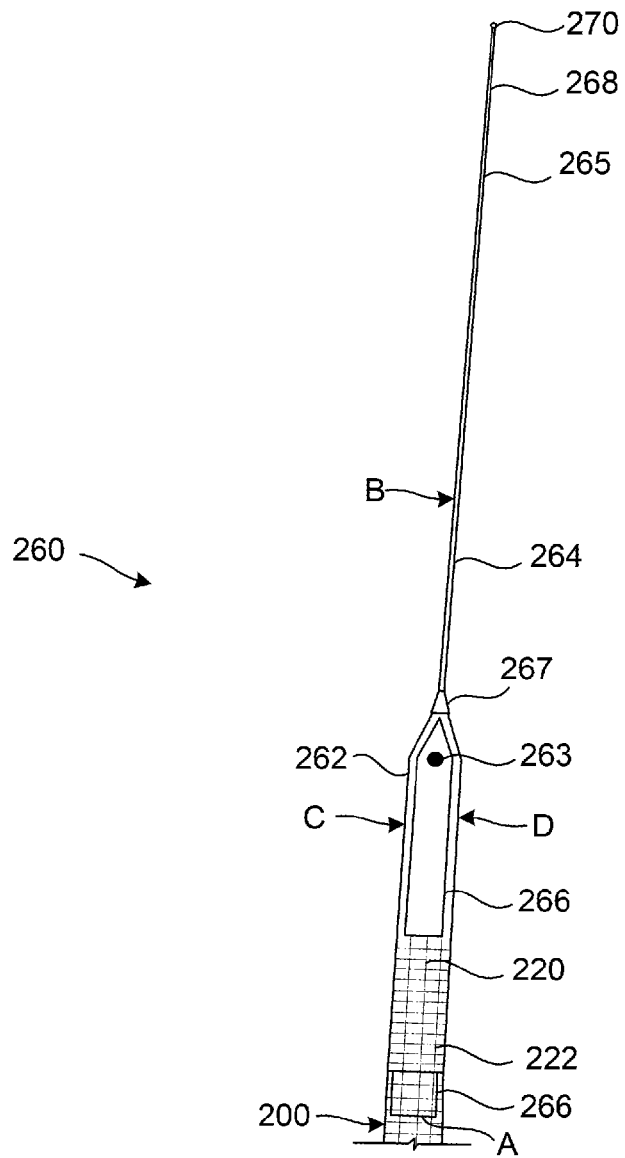
FIG. 4 is a top view of a portion of the implant of FIG. 2 coupled to a delivery assembly.

In some embodiments, a delivery assembly is used to facilitate the delivery of the implant into the body of the patient. FIG. 4 is a top view of a portion of the extension member 220 of the implant 200 coupled to a delivery assembly 260. The delivery assembly 260 is configured to assist in the implantation and placement of the implant 200 within the body of the patient. Although only one delivery assembly is illustrated, it should be understood that a delivery assembly may be associated with each of the arm portions 222 and 226 of the extension member 220. Additionally, it should be understood that any known delivery assembly and mechanism may be used to deliver and place the implant 200 within the body of the patient.

The delivery assembly includes a sleeve 262 disposed over the first arm portion 222. A dilator 264 defining a lumen is coupled to the first sleeve 262 by, for example, crimping, heat sealing, stitching, stretching, tip tipping, etc. Alternatively, the sleeve can be formed to include a portion that forms a tapered dilator. The dilator 264 can be used to expand or enlarge a passage during insertion through bodily tissue, to ease the transition to a cross-section or size of the sleeve 262. In some embodiments, the sleeve 262 is also tapered, which also helps provide a lead-in through the bodily tissue.

The sleeve 262 is secured to the first arm portion 222 with a suture 266. The suture 266 is looped through the first arm portion 222. In this embodiment, the suture 266 is weaved or threaded through the first arm portion 222. For example, as shown in FIG. 4, the suture 266 is weaved through the first arm portion at location A, as well as other locations along the first arm portion 222. The threading of the suture 266 through the first arm portion 222 can also help prevent stretching of the first arm portion 222 during implantation. The strands of the first suture 266 forming the loop through the first arm portion 222 extend through an interior lumen (not shown) of the dilator 264 and are crimped closed and heat bonded to an interior wall of the dilator 264 at, for example, a location B shown in FIG. 4, to maintain the first arm portion 222 within the sleeve 262 and the dilator 264.

The suture 266 can alternatively be coupled to the first arm portion 222 by, for example, crimping, heat sealing, stitching, stretching, tip tipping, etc. In some embodiments, a suture can be threaded to or secured to the first arm portion, for example by knotting.

The suture 266 includes a leader portion 268 that extends distally from the leading end 265 of the dilator 264. Alternatively, a separate suture can be coupled to and extend distally from the dilator. A needle 270 is coupled to a distal end of the leader portion 268 of the first suture 266. The needle 268 can be used to associate the implant 200 to a delivery device, as will be described in more detail below.

The sleeve 262 includes a separator 263 disposed between two strands of the suture 266 and near a distal end of the sleeve 262. The separator 263 maintains separation of the strands of the suture 266 within the sleeve 262. The separation of the strands of the suture 266 enables or helps facilitate a cut to be made through only a single strand of the suture 266 at, for example, location C or D, during removal of the sleeve 262 and the delivery assembly 260, as described in more detail below. In the illustrated embodiment, the separator 263 is a seal, which can be formed, for example, by heat stamping two sides of the sleeve 262 together. Other types of separators can alternatively be used, such as for example, a separate component coupled within the sleeve, or an adhesive can be used to couple the two sides of the sleeve together at a location between the strands.

The dilator 264 tapers from a first diameter at a trailing end 267 to a second, smaller diameter at a leading end 265. The first diameter can be, for example, between about 0.2 and 0.5 cm (0.08 to 0.2 inches) and the second diameter can be, for example, between about 0.03 to 0.2 cm (0.01 to 0.08 inches). For example, in some embodiments, the first diameter can be about 0.37 cm (0.15 inches) and the corresponding second diameter can be 0.03 cm (0.01 inches). The dilator 264 can be formed, for example, by molding, extruding, casting, sintering, forging, machining, or other known methods of manufacturing such medical devices.

Figure 5:
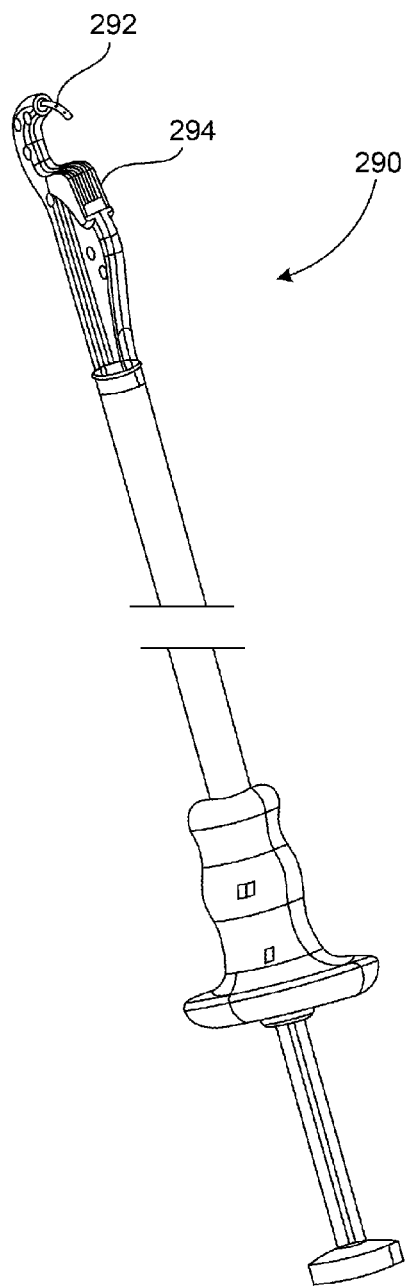
FIG. 5 is a perspective view of an instrument that may be used to deliver the implant of FIG. 2 into the body of a patient.

In some embodiments, a suturing delivery device 290, as shown in FIG. 5 is used to attach the implant 200 to the bodily tissue. For example, the needle 270 coupled to the first arm portion 222 is loaded into the carrier 292 (shown partially extended in FIG. 5) of the delivery device 290. The delivery device 290 can then be used to pass the needle 270 and the first arm portion 222 (with the sleeve 262 and the dilator 264 attached thereto) through bodily tissue of the patient, such as the sacrospinous ligament of the patient. Specifically, the carrier 292 of the delivery device 290 is inserted into a body of a patient through the vagina and positioned adjacent the sacrospinous ligament. The carrier 292 is then actuated (for example, by actuating a plunger at an end portion of the delivery device 290) such that the carrier 292 extends and the needle 270 pierces through the sacrospinous ligament. The needle 270 and a distal end of the leader portion 268 of the suture 266 are caught or retrieved by a catch 294 of the delivery device 290 after passing through the sacrospinous ligament. The delivery device 290 is then removed through the vagina, and the needle 270 is removed from the catch 294. The sleeve 262 and the dilator 264 are pulled through the sacrospinous ligament. For example, the user can pull the leader portion 268 of the suture 266 or the dilator 264 through the sacrospinous ligament such that the first arm portion 222 is disposed within the sacrospinous ligament. This procedure is then repeated to deliver the second arm portion 226 into the sacrospinous ligament.

After the first arm portion 222 and the second arm portion 226 are disposed within the sacrospinous ligament, the arm portions 222 and 226 can be adjusted to position and tension the body member 210 within the body of the patient. Each arm portion 222 and 226 can be delivered sequentially using the same delivery device, or separate delivery devices can be used for some or all of the arm portions. The arm portions 222 and 226 (with sleeves) can be tensioned using visual guidance as the user observes the positioning of the body member 210 for the correct tension through the vaginal incision. Additionally, the user may observe the center marking 230 of the extension member 220 to correctly place the implant 200 within the body of the patient.

After the arm portions 222 and 226 have been placed through the sacrospinous ligament and adjusted as described above, the delivery assemblies can be removed from the arm portions 222 and 226. For example, as shown in FIG. 4, to remove the delivery assembly 260 from the arm portion 222, a portion of the sleeve 262 and one strand of the loop of the suture 266 within the sleeve 262 can be cut, for example, at location C or D. Because the arm portion 222 is coupled to the sleeve 262 via the suture 266, cutting through a portion of the sleeve 262, and one strand of the loop of the suture 266, the sleeve 262 will be freely movable relative to the first arm portion 222. The sleeve 262 (and dilator 262 which is coupled to the sleeve 262) can then be pulled off of the first arm portion 222 by pulling on the sleeve 262 and the uncut strand of the suture 266. The cut portion of the suture 266 will also be free to pull through the first arm portion 222. Thus, the suture 266 remains secured to the sleeve 262 and will simply unravel or unthread itself from the first arm portion 222. With the sleeve 262 removed from the first arm portion 222, the tangs of the first arm portion 222 can engage the surrounding tissue into which the first arm portion 222 is placed to couple the first arm portion 222 to the bodily tissue (the sacrospinous ligament).

After the arm portions 222 and 226 are secured within the sacrospinous ligament, excess portions of the arm portions 222 and 226 can be trimmed as needed. For example, if a portion of the first arm portion 222 extends through the sacrospinous ligament after the arm portions 222 and 226 are placed within the sacrospinous ligament, the portion of the first arm portion 222 extending through the sacrospinous ligament can be removed.

Although attachment of the arm portions 222 and 226 were described in detail as being inserted into and coupled to the sacrospinous ligament, the arm portions 222 and 226 (or additional arm portions of the implant) can be secured within a pelvic region (or other portions of the body of the patient) at various different tissue sites. For example, the arm portions of the implant can be placed, for example, in a coccygeus muscle. In other embodiments, the arm portions are placed through, endopelvic fascia, or through tissue or ligaments near or in the pubococcygeus muscle, puborectalis muscle, distal tendineus arch of levator ani muscle or other tissue locations within a pelvic region. In still other embodiments, the arm portions are placed, for example, within an illiococcygeus muscle, or an arcus tendineus.

In some embodiments, a portion of the body member 210 is separately attached to a tissue within the pelvic region. Said another way, a portion of the body member 210 can be secured by means additional to the arm portions 222 and 226. For example, a suture can be threaded through the body member 210 and attached to adjacent pelvic tissue, such as the vaginal apex. This can provide additional support for the body member 210.

Figure 6:
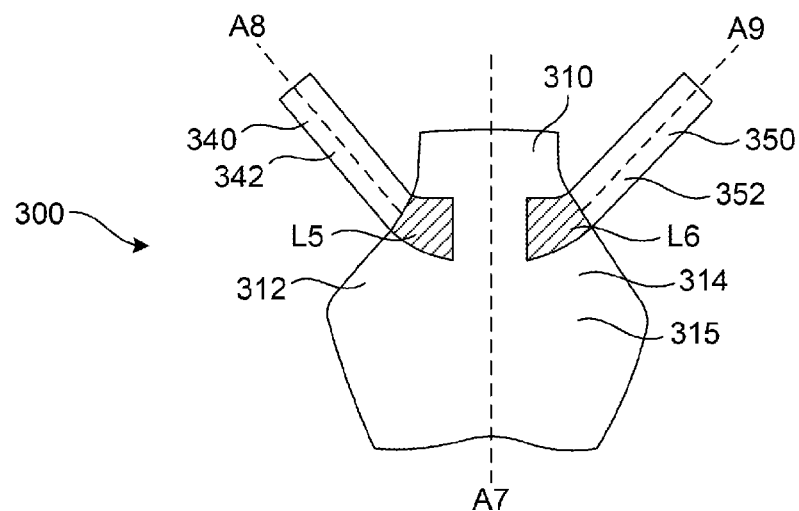
FIG. 6 is a top view of an implant according to an embodiment of the invention.

FIG. 6 is a top view of an implant 300 according to an embodiment. The implant 300 includes a body member 310, a first arm member 340, and a second arm member 350. In this embodiment, the first arm member 340 and the second arm member 350 are not coupled together. Rather each of the first arm member 340 and the second arm member 350 are individually coupled to the body member 310.

The body member 310 has a first side portion 312 and a second side portion 314 and defines a longitudinal axis A7. The body member 310 also includes an upper surface 315 and a lower surface (not illustrated) opposite the upper surface 315. In the illustrated embodiment, the body member 310 is formed of or includes a natural material.

The first arm member 340 is formed of or includes a synthetic material, such as a polypropylene mesh or other biocompatible synthetic material. The first arm member 340 extends from the first side portion 312 of the body member 310 along an axis A8 that is non-perpendicular to the longitudinal axis A7 of the body member 310.

The first arm member 340 includes an upper surface 342 and a lower surface (not illustrated) opposite the upper surface 342. The first arm member 340 is coupled to the body member 310 such that the lower surface of the first arm member 340 abuts or contacts the upper surface 315 of the body member 310. In the illustrated embodiment, the first arm member 340 is coupled to the body member 310 via stitching at a location L5. In other embodiments, the first arm member 340 is coupled to the body member 310 via another known coupling technique or mechanism.

The second arm member 350 is formed of or includes a synthetic material, such as a polypropylene mesh or other biocompatible synthetic material. In some embodiments, the first arm member and the second arm member are formed of or include the same material. The second arm member 350 extends from the second side portion 314 of the body member 310 along an axis A9 that is non-perpendicular to the longitudinal axis A7 of the body member 310. Axis A9 is different than axis A8 defined by the first arm member 340 and is non-perpendicular and non-parallel to axis A8. Axis A9 is angled with respect to axis A8.

The second arm member 350 includes an upper surface 352 and a lower surface (not illustrated) opposite the upper surface 352. The second arm member 350 is coupled to the body member 310 such that the lower surface of the second arm member 350 abuts or contacts the upper surface 315 of the body member 310. In the illustrated embodiment, the second arm member 350 is coupled to the body member 310 via stitching at a location L6. In other embodiments, the second arm member 350 is coupled to the body member 310 via another known coupling technique or mechanism.

In some embodiments, the implant 300 may be formed or manufactured by coupling an extension member to a body member at two different locations and then cutting or otherwise removing the portion of the extension member disposed between the first coupling location and the second coupling location.

Figure 7:
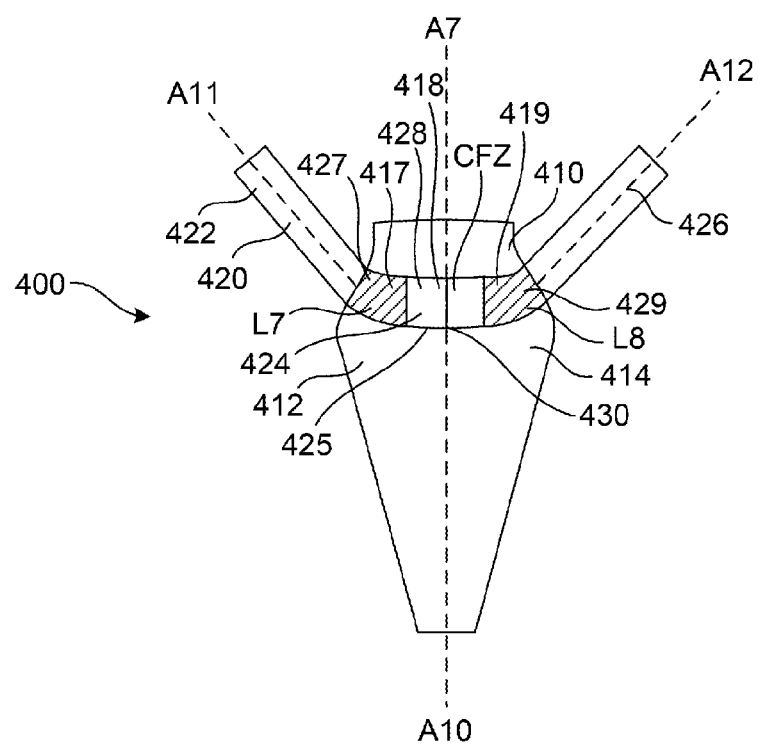
FIG. 7 is a top view of an implant according to an embodiment of the invention.
Figure 8:
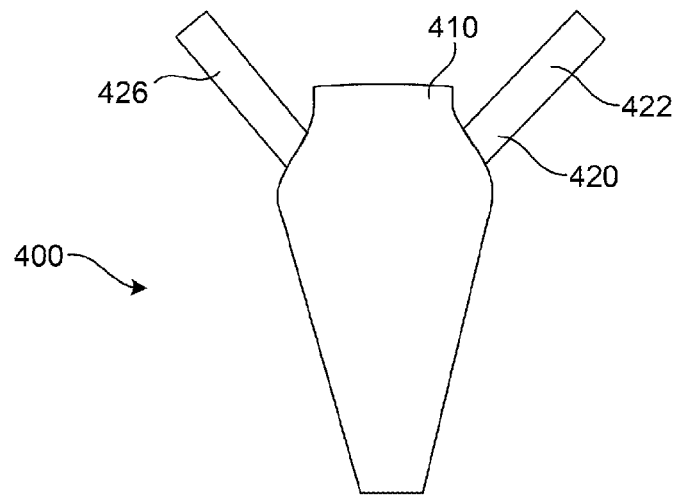
FIG. 8 is a bottom view of the implant of FIG. 7.

FIG. 7 is a top view of an implant 400 according to an embodiment. FIG. 8 is a bottom view of the implant 400. The implant 400 includes a body member 410 and an extension member 420. The implant 400 is configured to be disposed within a body of a patient and to provide support to a portion of the body of the patient. Specifically, the implant 400 is configured to be disposed in a posterior portion of a pelvic region of a patient. For example, the implant 400 may be placed in the posterior portion of a pelvic region of a patient and configured to support, for example, a uterus or rectum of the patient. Specifically, the body member 410 may be disposed proximate uterus and/or the rectum and the extension member may extend to the sacrospinous ligament of the patient to provide support to the implant 400 and to help retain the implant 400 in position within the body of the patient.

The body member 410 is formed of a first material and includes a first side portion 412 and a second side portion 414. The body member 410 defines a longitudinal axis A10.

In the illustrated embodiment, the body member 410 is formed of a biologic or natural material. For example, in some embodiments, the body member 410 is formed of or includes bovine dermis. In other embodiments, the body member is formed of or includes porcine dermis, human cadaveric dermis, or another collagen source. In some embodiments, the body member 410 is formed of Xenform® or Repliform® as sold by Boston Scientific Corporation.

The extension member 420 has a first arm portion 422, a second arm portion 426, and a mid-portion 424 disposed between the first arm portion 422 and the second arm portion 426. The extension member 420 is coupled to the body member 410 such that the mid-portion 424 extends from the first side portion 412 of the body member 410 to the second side portion 414 of the body member 410.

In some embodiments, the extension member 420 is formed of or includes a material that is different than the material that forms or is included in the body member 410. In the illustrated embodiment, the extension member 420 is formed of a synthetic material. For example, in some embodiments, the extension member 420 is formed of or includes a mesh material, such as a polypropylene mesh. In other embodiments, the extension member 420 is formed of or includes a natural material.

The first arm portion 422 of the extension member extends from the first side portion 412 of the body member 410 in a first direction. Specifically, the first arm portion 422 extends from the first side portion 412 of the body member 410 along an axis A11 that is non-perpendicular to a longitudinal axis A10 defined the body member 410.

In the illustrated embodiment, the second arm portion 426 extends from the second side portion 414 of the body member 410 along an axis A12 that is non-perpendicular to a longitudinal axis A10 defined the body member 410. The axis A12 is different and non-parallel to axis A11 defined by the first arm portion 422.

In the illustrated embodiment, the first arm portion 422 and the second arm portion 426 of the extension member 420 are substantially linear. Additionally, in the illustrated embodiment, the mid-portion 424 of the extension member 420 includes a curved portion 425.

The extension member 420 is coupled to the body member 410 such that a first surface of the extension member 420 is disposed adjacent to a first surface of the body member 410. In other words, as best illustrated in FIGS. 7 and 8, the extension member 420 overlays or overlaps a portion of the body member 410. Specifically, the mid-portion 424 of the extension member 420 is on top of the body member 410 and visible in FIG. 7, but is below the body member 420 and not visible in FIG. 8. Accordingly, a physician may place the implant 400 within the body such that the body member 410 (rather than the side of the implant that includes the body member 410 and the extension member 420) is disposed adjacent or contacting the incision created to place the implant 400. In some embodiments, this may help reduce tissue erosion at or near the incision or vaginal wall.

The extension member 420 is coupled to the body member 410 at a first location L7 and at a second location L8 different from and spaced from the first location L7. In the illustrated embodiment, the first location L7 and the second location L8 are disposed proximate opposite side portions 412 and 414 of the body member 410, respectively.

The mid-portion 424 of the extension member 420 includes a first portion 427, a second portion 429, and a middle portion 428 disposed between the first portion 427 and the second portion 429. The first portion 427 is coupled to the body member 410 at a first coupling location 417 of the body member 410. The second portion 429 is coupled to the body member 410 at a second coupling location 419 of the body member 410. The middle portion 428 of the extension member 420 is disposed adjacent to the body member 410 but is not coupled to the body member 410. Specifically, the middle portion 428 of the extension member 420 is not directly coupled to the body member 410. Accordingly, the implant 400 includes a coupling free zone CFZ (and the body member 410 includes a coupling-free location 418). In the illustrated embodiment, the coupling-free location 418 of the body member 410 is located along the longitudinal axis A10 defined by the body member 410. Accordingly, the coupling free zone CFZ of the implant 400 may be disposed within the body of the patient adjacent the incision location and may help prevent (or be less likely to cause) tissue erosion.

The extension member 420 may be coupled to the body member 410 using any known method. In the illustrated embodiment, the extension member 420 is sewn to the body member 410.

In the illustrated embodiment, the extension member 420 includes a centering mark 430. The centering mark or stripe 430 may be used to facilitate the accurate or correct placement of the implant 400 within the body of the patient. In some embodiments, the centering mark 430 is an ink stripe, such as a blue stripe. In other embodiments, the centering mark 430 is a different type of mark, such as a colored suture or the like.

Figure 9:
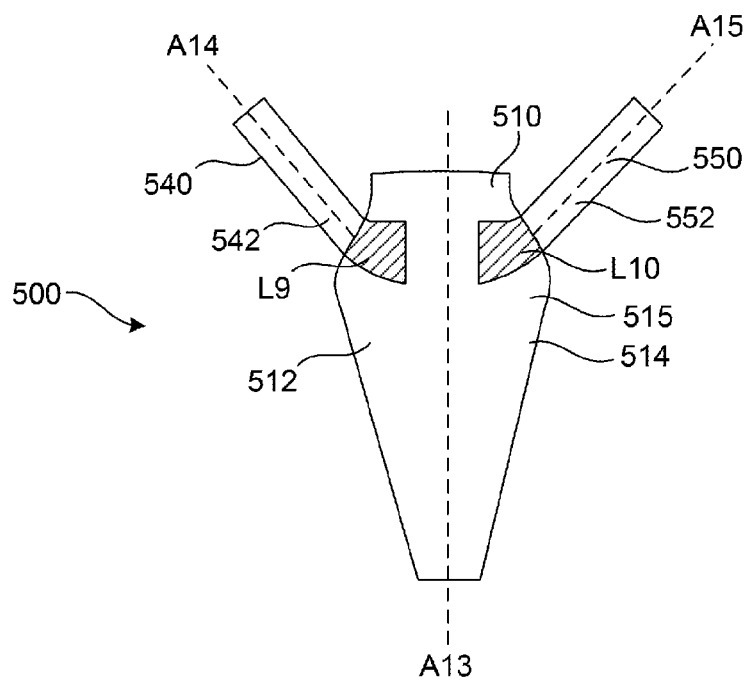
FIG. 9 is a top view of an implant according to an embodiment of the invention.

FIG. 9 is a top view of an implant 500 according to an embodiment. The implant 500 includes a body member 510, a first arm member 540, and a second arm member 550. In this embodiment, the first arm member 540 and the second arm member 550 are not coupled together. Rather each of the first arm member 540 and the second arm member 550 are individually coupled to the body member 510.

The body member 510 has a first side portion 512 and a second side portion 514 and defines a longitudinal axis A13. The body member 510 also includes an upper surface 515 and a lower surface (not illustrated) opposite the upper surface 515. In the illustrated embodiment, the body member 510 is formed of or includes a natural material.

The first arm member 540 is formed of or includes a synthetic material, such as a polypropylene mesh or other biocompatible synthetic material. The first arm member 540 extends from the first side portion 512 of the body member 510 along an axis A14 that is non-perpendicular to the longitudinal axis A13 of the body member 510.

The first arm member 540 includes an upper surface 542 and a lower surface (not illustrated) opposite the upper surface 542. The first arm member 540 is coupled to the body member 510 such that the lower surface of the first arm member 540 abuts or contacts the upper surface 515 of the body member 510. In the illustrated embodiment, the first arm member 540 is coupled to the body member 510 via stitching at a location L9. In other embodiments, the first arm member 540 is coupled to the body member 510 via another known coupling technique or mechanism.

The second arm member 550 is formed of or includes a synthetic material, such as a polypropylene mesh or other biocompatible synthetic material. In some embodiments, the first arm member and the second arm member are formed of or include the same material. The second arm member 550 extends from the second side portion 514 of the body member 510 along an axis A15 that is non-perpendicular to the longitudinal axis A13 of the body member 510. Axis A15 is different than axis A14 defined by the first arm member 540 and is non-perpendicular and non-parallel to axis A13. Axis A15 is angled with respect to axis A14.

The second arm member 550 includes an upper surface 552 and a lower surface (not illustrated) opposite the upper surface 552. The second arm member 550 is coupled to the body member 510 such that the lower surface of the second arm member 550 abuts or contacts the upper surface 515 of the body member 510. In the illustrated embodiment, the second arm member 550 is coupled to the body member 510 via stitching at a location L10. In other embodiments, the second arm member 550 is coupled to the body member 510 via another known coupling technique or mechanism.

In some embodiments, the implant 500 may be formed or manufactured by coupling an extension member to a body member at two different locations and then cutting or otherwise removing the portion of the extension member disposed between the first coupling location and the second coupling location.

Figure 10:
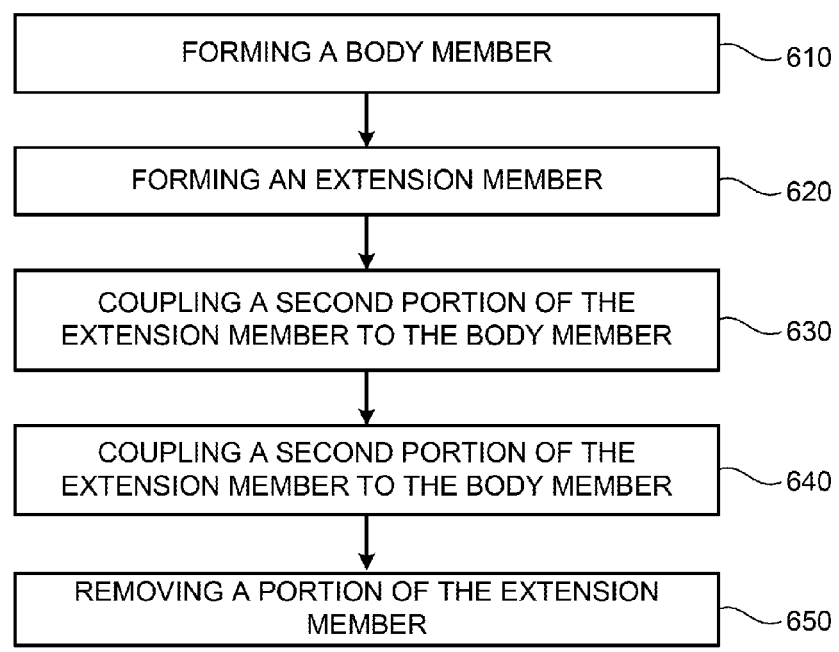
FIG. 10 is a flow chart of a method for making an implant according to an embodiment of the invention.

FIG. 10 is a flow chart of a method for forming an implant according to an embodiment. At step 610 a body member of an implant is formed. In some embodiments, the body member is formed of a natural or biologic material using known methods. For example, the body member may be formed by cutting a sheet of natural material into a desired shape.

At step 620, an extension member is formed. In some embodiments, the extension member is formed of a synthetic material using known methods. For example, the extension member may be formed by forming a synthetic mesh sheet and cutting the sheet to the desired shape.

At step 630, a first portion of the extension member is coupled to the body member at a first location. In some embodiments, the extension member is overlaid or disposed on top of a portion of the body member, and the first portion of the extension member is sewn to the body member at a first location. In other embodiments, another known method of coupling is used to couple the first portion of the extension member to the body member.

At step 640, a second portion of the extension member is coupled to the body member at a second location different and spaced from the first location. In some embodiments, the extension member is sewn to the body member. For example, a machine may be used to sew the extension member to the body member or the extension member may be hand sewn to the body member.

In some embodiments, at step 650, a portion of the extension member disposed between the first coupling location and the second coupling location is removed from the implant. For example, in some embodiments, the portion of the extension member disposed between the first coupling location and the second coupling location is cut (for example, via a knife or scissors) and removed from the implant.

In some embodiments, an implant includes a body member formed of a first material and having a first side portion and a second side portion and an extension member formed of a second material different than the first material. The extension member has a first arm portion, a second arm portion, and a mid-portion disposed between the first arm portion and the second arm portion. The mid-portion extends from the first side portion of the body member to the second side portion of the body member. The first arm portion extends from the first side portion of the body member along a first axis. The second arm portion extends from the second side portion of the body member along a second axis different than the first axis.

In some embodiments, the extension member is coupled to the body member at a first location and a second location different than the first location. In some embodiments, the mid-portion of the extension member includes a first portion, a second portion, and a middle portion. The first portion of the mid-portion of the extension member is coupled to the body member. The second portion of the mid-portion of the extension member is coupled to the body member. The middle portion of the mid-portion of the extension member is disposed adjacent the body portion and uncoupled to the body portion.

In some embodiments, the body member includes a first coupling location, a second coupling location, and a coupling-free location disposed between the first coupling location and the second coupling location. The body member is coupled to a portion of the extension member at the first coupling location. The body member is coupled to a portion of the extension member at the second coupling location. The body member is disposed adjacent and uncoupled to the extension member at the coupling-free location.

In some embodiments, the first material is a biologic material. In some embodiments, the second material is a synthetic material. In some embodiments, the first arm portion of the extension member is substantially linear. In some embodiments, the mid-portion of the extension member includes a curved portion.

In some embodiments, the implant is configured to be disposed within a pelvic region of a patient and to provide support to a portion of a body of the patient.

In some embodiments, an implant includes a body member formed of a first material and having a first side portion and a second side portion and an extension member formed of a second material different than the first material. The extension member has a first arm portion, a second arm portion, and a mid-portion disposed between the first arm portion and the second arm portion. The mid-portion extends from the first side portion of the body member to the second side portion of the body member. The first arm portion extends from the first side portion of the body member and the second arm portion extends from the second side portion of the body member. The body member includes a first coupling location, a second coupling location, and a coupling-free location disposed between the first coupling location and the second coupling location. The body member is coupled to a portion of the extension member at the first coupling location. The body member is coupled to a portion of the extension member at the second coupling location. The body member is disposed adjacent and uncoupled to the extension member at the coupling-free location.

In some embodiments, the first material is a biologic material. In some embodiments, the second material is a synthetic material. In some embodiments, the first arm portion of the extension member is substantially linear. In some embodiments, the mid-portion of the extension member includes a curved portion. In some embodiments, the implant is configured to be disposed within a pelvic region of a patient and to provide support to a portion of a body of the patient.

In some embodiments, an implant includes a body member formed of a first material and having a first side portion and a second side portion, the body member having an upper surface and a lower surface, a first arm member formed of a second material different than the first material, the first arm member having an upper surface and a lower surface, the lower surface of the first arm member being coupled to the upper surface of the body member, the first arm member extending from the first side portion of the body member along a first axis, and a second arm member formed of the second material, the second arm member having an upper surface and a lower surface, the lower surface of the second arm member being coupled to the upper surface of the body member, the second arm member extending from the second side portion of the body member along a second axis different than the first axis.

In some embodiments, the first material is a biologic material. In some embodiments, the second material is a synthetic material.

In some embodiments, a method of forming an implant includes coupling a first portion of an extension member to a first portion of a body member; coupling a second portion of an extension member to a second portion of a body member; and removing a portion of the extension member disposed between the first portion of the extension member and the second portion of the extension member.

In some embodiments, the removing includes cutting the extension member.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:
1. An implant, comprising:
   a body member formed of a first material and having a first side portion defining a first edge and a second side portion defining a second edge, the body member including a narrow portion and a wide portion having a width greater than the narrow portion, the body member including a first surface, and a second surface opposite to the first surface; and
   an extension member formed of a second material different than the first material, the extension member having a first arm portion, a second arm portion, and a mid-portion disposed between the first arm portion and the second arm portion, the mid-portion extending across a width of the first surface of the body member from the first edge of the body member to the second edge of the body member, the mid-portion being sewn to the body member at a first location on the body member, the mid-portion being sewn to the body member at a second location on the body member, wherein a sewn-free location on the body member extends between the first location and the second location, the first arm portion extending from the first side portion of the body member along a first axis, the first arm portion extending from the narrow portion of the body member, the second arm portion extending from the second side-portion of the body member along a second axis different than the first axis, the second arm portion extending from the narrow portion of the body member, wherein the mid-portion of the extension member includes a first portion, a second portion, and a middle portion disposed between the first portion and the second portion, each of the first portion, the second portion, middle portion of the mid-portion of the extension member includes a curved portion, and the middle portion of the mid-portion is the sewn-free location having portions on each side of a longitudinal axis defined by the body member.

2. The implant of claim 1, wherein the first location and the second location are disposed on the first surface on the narrow portion of the body member, and the first location is disposed a distance from the second location.

3. The implant of claim 1, wherein the first portion of the mid-portion of the extension member is coupled to the first surface of the body member, the second portion of the mid-portion of the extension member is coupled to the first surface of the body member, the middle portion of the mid-portion of the extension member is disposed adjacent the first surface of the body portion and uncoupled to the first surface of the body member.

4. The implant of claim 1, wherein the body member is sewn to a portion of the extension member at the first location, the body member being sewn to a portion of the extension member at the second location, the body member being disposed adjacent and not sewn to the extension member at the sewn-free location.

5. The implant of claim 1, wherein the first material is a biologic material.

6. The implant of claim 1, wherein the second material is a synthetic material.

7. The implant of claim 1, wherein the first arm portion of the extension member is substantially linear.

8. The implant of claim 1, wherein the implant is configured to be disposed within a pelvic region of a patient and to provide support to a portion of a body of the patient.

9. An implant, comprising:
a body member formed of a first material and having a first side portion defining a first edge and a second side portion defining a second edge, the body member including a first surface, and a second surface opposite to the first surface; and
an extension member formed of a second material different than the first material, the extension member having a first arm portion, a second arm portion, and a mid-portion disposed between the first arm portion and the second arm portion, the mid-portion extending across a width of the first surface of the body member from the first edge of the body member to the second edge of the body member, the first arm portion extending from the first side portion of the body member, the second arm portion extending from the second side portion of the body member, the mid-portion being coupled to the body member with a biocompatible adhesive at a first location on the body member, the mid-portion being coupled to the body member with the biocompatible adhesive at a second location on the body member, wherein an adhesive-free location extends on the body member between the first location and the second location, the body member including a narrow portion and a wide portion having a width greater than the narrow portion, the first arm portion of the extension member extending from the narrow portion of the body member, the second arm portion extending from the narrow portion of the body member, wherein the body member includes a first end portion, a second end portion, and a longitudinal axis extending between the first end portion and the second end portion, the mid-portion of the extension member including a first curved portion disposed on one side of the longitudinal axis, and a second curved portion disposed on another side of the longitudinal axis, the first curved portion curving towards the first arm portion and the first end portion, the second curved portion curving towards the second arm portion and the first end portion.

10. The implant of claim 9, wherein the first material is a biologic material.

11. The implant of claim 9, wherein the second material is a synthetic material.

12. The implant of claim 9, wherein the first arm portion of the extension member is substantially linear.

13. The implant of claim 9, wherein the implant is configured to be disposed within a pelvic region of a patient and to provide support to a portion of a body of the patient.

14. A method of forming an implant, comprising:
coupling a first portion of a mid-portion of an extension member to a first portion of a body member, the body member having a first side portion defining a first edge and a second side portion defining a second edge, the body member including a first surface, and a second surface opposite to the first surface, the extension member having a first arm portion extending from the first side portion, a second arm portion extending from the second side portion, the mid-portion disposed between the first arm portion and the second arm portion;
coupling a second portion of the mid-portion of the extension member to a second portion of a body member such that the mid-portion extends across a width of the body member on the first surface of the body member from the first edge to the second edge, the mid-portion of the extension member including a curved portion disposed on both sides of a longitudinal axis of the body member; and
removing at least a portion of the curved portion of the mid-portion of the extension member, the curved portion being disposed between the first portion of the mid-portion of the extension member and the second portion of the mid-portion of the extension member.

15. The method of claim 14, wherein the removing includes cutting the middle portion of the mid-portion of the extension member.

* * * * *